(12) United States Patent
Osypka

(10) Patent No.: US 10,716,552 B2
(45) Date of Patent: Jul. 21, 2020

(54) IMPLANTABLE SEALING DEVICE

(71) Applicant: Peter Osypka Stiftung, Grenzach-Wyhlen (DE)

(72) Inventor: Peter Osypka, Grenzach-Wyhlen (DE)

(73) Assignee: Peter Osypka Stiftung, Grenzach-Wyhlen (DE)

( * ) Notice: Subject to any disclaimer, the term of this patent is extended or adjusted under 35 U.S.C. 154(b) by 268 days.

(21) Appl. No.: 15/963,722

(22) Filed: Apr. 26, 2018

(65) Prior Publication Data

US 2018/0235588 A1 Aug. 23, 2018

Related U.S. Application Data

(60) Continuation-in-part of application No. 15/816,217, filed on Nov. 17, 2017, which is a division of
(Continued)

(30) Foreign Application Priority Data

Dec. 10, 2012 (EP) .................................... 12008240

(51) Int. Cl.
*A61B 17/00* (2006.01)
*A61N 1/05* (2006.01)

(52) U.S. Cl.
CPC ........ *A61B 17/0057* (2013.01); *A61N 1/0587* (2013.01); *A61B 2017/00243* (2013.01);
(Continued)

(58) Field of Classification Search
CPC .......... A61B 17/0057; A61B 17/12172; A61B 17/12122; A61B 17/12159;
(Continued)

(56) References Cited

U.S. PATENT DOCUMENTS 3,874,388 A * 4/1975 King .................. A61B 17/0057
606/232
5,171,259 A * 12/1992 Inoue ................. A61B 17/0057
606/213
(Continued)

FOREIGN PATENT DOCUMENTS

DE 202010011724 U1 11/2010
EP 2340770 A1 7/2011
WO WO-2011/156782 A1 12/2011

OTHER PUBLICATIONS

European Search Report dated May 29, 2013 issued in corresponding European Patent Application No. 12008240.9.

*Primary Examiner* — Katherine H Schwiker
(74) *Attorney, Agent, or Firm* — Locke Lord LLP; Scott D. Wofsy

(57) ABSTRACT

A method for sealing a tissue opening includes inserting a trocar tube including a folded sealing device disposed within the trocar, and guiding the trocar tube through an opening in a myocardium into a patient's ventricle, the sealing device can include an elongated elastic member having a distal and a proximal end, a proximal umbrella shaped braiding extending radially from the elongated elastic member, the proximal braiding being positioned at the proximal end of the elastic member, wherein the proximal braiding includes a proximal disc disposed therein having a proximal disc thread disposed therethrough such that a user can pull the proximal braiding, and a distal umbrella shaped braiding extending radially from the elongated elastic member and being positioned at the distal end of the elastic member opposite to the proximal braiding.

20 Claims, 8 Drawing Sheets

Related U.S. Application Data application No. 14/101,013, filed on Dec. 9, 2013, now abandoned.

(52) U.S. Cl.
CPC ............... *A61B 2017/00575* (2013.01); *A61B 2017/00579* (2013.01); *A61B 2017/00592* (2013.01); *A61B 2017/00597* (2013.01); *A61B 2017/00606* (2013.01); *A61B 2017/00615* (2013.01); *A61B 2017/00623* (2013.01); *A61B 2017/00867* (2013.01); *A61N 1/0595* (2013.01)

(58) Field of Classification Search
CPC ........ A61B 17/12163; A61B 17/12168; A61B 17/12177; A61B 2017/00592; A61B 2017/00606; A61B 2017/00575; A61B 2017/00597; A61B 2017/00623; A61B 2017/0495; A61B 2017/0496

See application file for complete search history.

(56) References Cited

U.S. PATENT DOCUMENTS

| | | | |
|---|---|---|---|
| 2004/0002763 A1* | 1/2004 | Phillips | A61B 17/0401 623/17.16 |
| 2004/0220610 A1 | 11/2004 | Kreidler et al. | |
| 2005/0177182 A1 | 8/2005 | van der Burg et al. | |
| 2006/0229670 A1 | 10/2006 | Bates | |
| 2007/0208376 A1 | 9/2007 | Meng | |
| 2008/0033425 A1 | 2/2008 | Davis et al. | |
| 2008/0091235 A1* | 4/2008 | Sirota | A61B 17/0057 606/215 |
| 2008/0200945 A1 | 8/2008 | Amplatz et al. | |
| 2010/0234878 A1* | 9/2010 | Hruska | A61B 17/0057 606/213 |
| 2011/0184439 A1* | 7/2011 | Anderson | A61B 17/0057 606/151 |
| 2012/0065667 A1* | 3/2012 | Javois | A61B 17/12122 606/213 |
| 2013/0138144 A1* | 5/2013 | Yribarren | A61B 17/12109 606/213 |
| 2014/0303603 A1* | 10/2014 | Kullas | A61M 25/0023 604/540 |
| 2015/0157436 A1* | 6/2015 | Bailly | A61B 17/0057 606/151 |
| 2016/0074023 A1* | 3/2016 | Sakamoto | A61B 17/12172 606/200 |
| 2018/0103956 A1* | 4/2018 | Sakamoto | A61B 17/0057 |

* cited by examiner

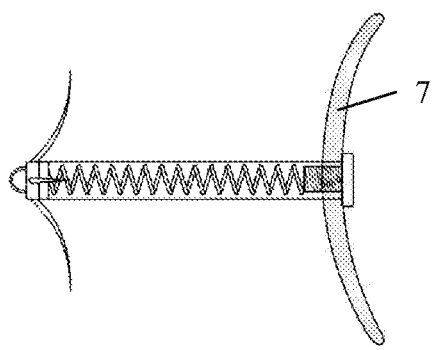
Fig.7c
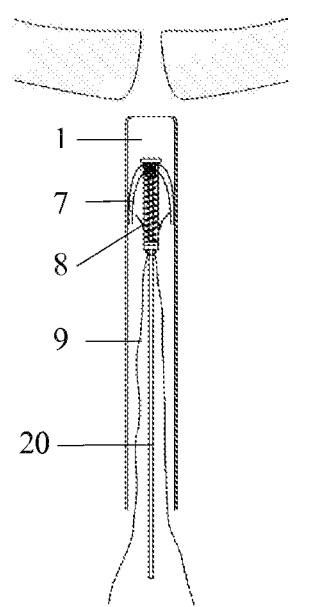
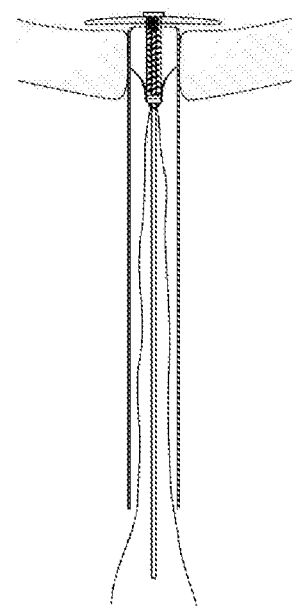
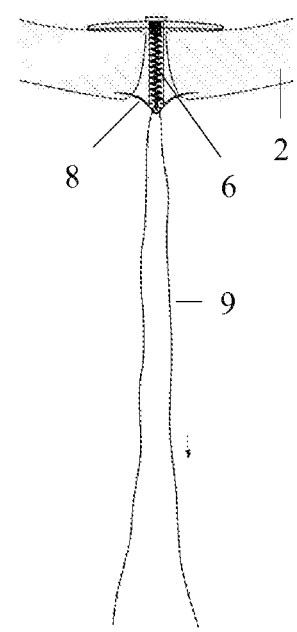
Fig. 8            Fig. 9            Fig. 10

IMPLANTABLE SEALING DEVICE

CROSS-REFERENCE TO RELATED APPLICATIONS

This application is a continuation-in-part of U.S. patent application Ser. No. 15/816,217 filed Nov. 17, 2017, which is a divisional of U.S. patent application Ser. No. 14/101,013 filed Dec. 9, 2013, which claims priority under 35 U.S.C. § 119(a) to European Patent Application No. EP12008240, filed with the European Patent Office on Dec. 10, 2012, the content of each of which is incorporated by reference herein in its entirety.

BACKGROUND OF THE INVENTION

1. Field of the Invention

The present disclosure relates to an implantable sealing device for sealing a tissue opening, more specifically a trocar tube opening in the left ventricle of the heart.

2. Description of Related Art

Deficient heart valves can be repaired or replaced using a variety of different types of heart valve surgeries. One general type of heart valve surgery involves an open-heart surgical procedure during which the heart is stopped and blood flow is controlled by a heart-lung bypass machine. This type of valve surgery is highly invasive and exposes the patient to a number of potential risks associated with use of the heart-lung machine.

Due to the drawbacks of open-heart surgical procedures, there has been an increased interest in minimally invasive and percutaneous replacement of cardiac valves. Such surgical techniques involve making a relatively small opening in the chest of the patient into which a valve assembly is inserted and delivered into the heart via the operating device of a so-called trocar tube. The minimally invasive methods include reduced pain due to smaller incisions and less bleeding, shorter recovery time, and, especially, avoid the use of a heart-lung machine.

Minimally invasive surgical procedures such as transcatheter aortic valve implantation (TAVI) and transapical aortic valve implantation (TAAVI) have become feasible alternatives to open techniques in high risk patients.

In the TAVI process, the artificial valve is attached to a compressed stent, the stent being attached to a balloon catheter. The balloon catheter is inserted in the femoral artery and guided into the heart to the area of the aortic valve. Once in position, the balloon is inflated to secure the valve in place.

In the TAAVI approach, the replacement valve is inserted through a small incision in the chest wall of a patient and the catheter is advanced through the apex of the heart. Like in the TAVI approach, a balloon catheter is inserted through an introducer, e.g. a trocar tube and guided into the heart to the area of the aortic valve. After valve deployment, the trocar tube is removed and the opening in the ventricular apex is sutured.

A problem in the transapical procedure is the haemostatic closure of the left ventricular apex. Frequently, a purse string suture is placed in the tissue prior to insertion of the trocar tube to facilitate closure after the procedure is complete. After removing the trocar tube the ends of the suture are drawn tight to close the wound. Due to the high pressure created by the contraction of the heart severe problems may occur when the suture is not tight or disrupts.

SUMMARY OF THE INVENTION

An object of the present disclosure is therefore to provide an improved device for sealing a tissue opening, especially a trocar tube opening in the myocardium after the transapical procedure of valve replacement. The device can not only seals the tissue opening itself, such that the primary bleeding is stopped, but also prevent secondary bleeding from occurring. The tissue opening should be tightly closed. Furthermore, the device is filigree and flexible in order to be able to follow the movement of the heart without the occurrence of structural damage such as e.g. cracks. The beating of the heart and the heart rate of the patient should not be affected. Due to its filigree construction the braiding can take the anatomical shape of the apex of the left ventricle, the place where the trocar is introduced.

A further object of the disclosure is to provide the above required device and to simultaneously provide a possibility to place heart wires in minimally invasive heart surgery procedures.

The sealing device can include a membrane coated braiding of fine threads. Furthermore a tensioning member and a fixing member are present for placing and anchoring the sealing device into the myocardium.

In some embodiments, a sealing device according to the present disclosure comprises an elongated elastic member having a distal and a proximal end, at least one sealing element in form of an umbrella shaped braiding having outside and inside faces, the braiding being positioned respectively at the distal and proximal ends of the elastic member, wherein the braiding includes a plurality of fine threads of a memory metal alloy and wherein at least one face of the braiding is coated by a membrane, and a fixing member being positioned respectively at the distal and proximal ends of the elastic member and being positioned opposite to the braiding.

The braiding may be very soft and flexible in order to avoid injuring the very soft heart tissue. The braiding is able to follow the movement of the heart. The braiding is adapted to the anatomical shape of the apex of the left ventricle and includes at least 30 fine threads, preferably 30 to 100 threads, more preferably 70 to 90 threads. The threads are 0.03 to 0.15 mm in diameter, preferably 0.05 to 0.13 mm in diameter; more preferably circa 0.1 mm in diameter. Due to the number of fine threads the device fulfills the requirement of flexibility and softness.

The umbrella shaped braiding is preferably made out of Nitinol threads thus allowing the self-deployment of the membrane coated braiding whereby the braiding is adapted to the shape of the apex of the left ventricle due to the shape memory properties of Nitinol.

The interaction of the sealing member, the elastic member, and the fixing member allows the immediate closure of the opening in the apex of the left ventricle. The immediate closure is beneficial due to the high pressure in the left ventricle created by the contraction of the heart and the strong movement of the heart. The sealing of the trocar tube opening in the myocardium starts immediately after the placing and fixing of the membrane coated braiding.

A preferred sealing device comprises an elongated elastic member having distal a and a proximal end, at least one sealing element in form of an umbrella shaped braiding having outside and inside faces, the braiding being positioned respectively at the distal and proximal ends of the elastic member, wherein the braiding includes at least 30 threads made of Nitinol, said threads being 0.03 to 0.15 mm in diameter and wherein at least one face of the braiding is coated by a membrane, and whereby in a position in use the braiding is adapted to the anatomical shape of the apex of the left ventricle, and a fixing member positioned respectively at the distal and proximal ends of the elastic member and being positioned opposite to the braiding.

At least one membrane coated braiding can be present. When additional sealing may be necessary a second membrane coated braiding may be present positioned opposite to the first membrane coated braiding.

The membrane coated braiding is preferably positioned at the distal end of the elastic member, thus being positioned at the inner side of the opening in the myocardium in the position of use as shown in FIG. 2.

Suitable membranes are made out of biocompatible plastic such as e.g. silicone or polyurethane, preferably silicone. It is important that the membrane is biocompatible and impervious to blood.

The coating is positioned respectively at the outside face or at inside face of the braiding, preferably at the outside face. If desired, both sides of the braiding may be coated.

The elongated elastic member is a tensioning element and may be a spring or a member made from elastic biocompatible material like rubber. The spring is preferably a coil spring made, for example, from stainless steel, MP35N or Nitinol.

The fixing member may be any known fixing member which may be deployed from a retracted to an extended position. Preferably the fixing member includes radially expandable arms, e.g. a pair of radially expandable arms which extend from the elongated elastic member. The arms are formed from a bio-compatible material, such as stainless steel, MP35N or Nitinol, preferably Nitinol. The fixing member is operatively associated with the elongated elastic member and is mounted for movement between a retracted position wherein the arms are disposed within the interior lumen of the trocar tube and an extended position wherein the arms extend radially outwardly to anchor the elastic member and thus to anchor the umbrella shaped membrane coated braiding in the myocardium thus sealing the opening in the myocardium. The radially expandable arms may be different in shape, whereby the shape may influence the anchor effect. Before use, the sealing device is folded and is disposed within the interior lumen of the trocar tube.

The disclosure further relates to a method for sealing a tissue opening, especially a trocar tube opening in the myocardium at the apex of the left ventricle comprising inserting a trocar tube including a folded sealing device as described herein and guiding the trocar tube through an opening in the myocardium into the patient's left ventricle, pushing the folded umbrella shaped and membrane coated braiding out of the trocar tube so that the umbrella moves from a folded into a deployed position whereas the fixation member remains inside the trocar tube, stretching the elastic member by means of a tensioning cord and pulling the pre-stretched elastic member out of the opening in the myocardium whereby the fixing member is placed against the tissue of the myocardium and moves from a folded into a deployed position, removing the trocar tube whereby the elastic member remains stretched, and removing the tension from the elastic member whereby the fixing member anchors in the tissue of the myocardium.

In accordance with at least one aspect of this disclosure, a method for sealing a tissue opening includes inserting a trocar tube including a folded sealing device disposed within the trocar, and guiding the trocar tube through an opening in a myocardium into a patient's ventricle, the sealing device can include an elongated elastic member having a distal and a proximal end, a proximal umbrella shaped braiding extending radially from the elongated elastic member, the proximal braiding being positioned at the proximal end of the elastic member, wherein the proximal braiding includes a proximal disc disposed therein having a proximal disc thread disposed therethrough such that a user can pull the proximal braiding, and a distal umbrella shaped braiding extending radially from the elongated elastic member and being positioned at the distal end of the elastic member opposite to the proximal braiding.

The method includes pushing the distal braiding out of the trocar tube so that the distal braiding moves from a folded position into a deployed position to contact an inside tissue wall, whereas the proximal braiding remains inside the trocar tube, stretching the elastic member by pulling the proximal disc thread engaged with the proximal disc such that the proximal braiding is located out of the opening in the myocardium when the proximal braiding is removed from the trocar, and removing the proximal braiding from the trocar while the trocar is located out of the opening in the myocardium such that the proximal braiding moves from a folded position into a deployed position and presses against an outside tissue wall.

Removing the proximal braiding includes removing the trocar after the distal braiding is contacting the inside tissue wall. The distal braiding can include a distal disc disposed therein.

The sealing device can include one or more threads disposed through the distal disc such that the one or more threads can pull on the distal disc and/or the distal braiding. The one or more threads can be two threads, for example. Any suitable number of threads is contemplated herein. The one or more threads can also be disposed through the proximal disc such that the one or more threads can be pulled through the proximal disc. The proximal braiding and/or the distal braiding can include a plurality of fine threads of a memory metal alloy and wherein at least one face is coated by a membrane.

The method can include pulling the one or more threads after removing the proximal braiding from the trocar to press tissue between the distal and proximal braiding. In certain embodiments, the method can include knotting the one or more threads to the proximal disc and/or the proximal braiding to fix the relative position of the distal and proximal braiding.

The method can include using a multi-lumen catheter to insert one or more temporary electrodes and the trocar into the myocardium, and stimulating the myocardium using the one or more temporary electrodes. The method can include using at least one of the distal braiding or the proximal braiding as an indifferent electrode electrically connected to an external pacemaker.

In accordance with at least one aspect of this disclosure, a tissue sealing device can include an elongated elastic member having a distal and a proximal end, a proximal umbrella shaped braiding extending radially from the elongated elastic member, the proximal braiding being positioned at the proximal end of the elastic member, wherein the proximal braiding includes a proximal disc disposed therein having a proximal disc thread disposed therethrough such that a user can pull the proximal braiding, and a distal umbrella shaped braiding extending radially from the elongated elastic member and being positioned at the distal end of the elastic member opposite to the proximal braiding. In certain embodiments, the distal braiding can include a distal disc disposed therein.

The sealing device can include one or more threads disposed through the distal disc such that the one or more threads can pull on the distal disc and/or the distal braiding. The one or more threads can include two threads. The two threads include double threads, for example. The one or more threads can also disposed through the proximal disc such that the one or more threads can be pulled through the proximal disc.

The elastic member can define a tube, for example. The one or more threads can be disposed in a wall of the elastic member between the proximal end and the distal end of the elastic member. The elastic member can include one or more valves disposed within the tube. The proximal and/or distal discs can include a central hole therethrough to form a washer shape, e.g., to allow fluid communication or instrument insertion through the tube and/or valves therein. The proximal braiding and/or the distal braiding include a plurality of fine threads of a memory metal alloy and wherein at least one face is coated by a membrane.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIGS. 7a, 7b and 7c show the sealing system in detail;

FIGS. 8, 8a, 9, 9a and 10, 10a, show the steps of placing and affixing the sealing system;

DETAILED DESCRIPTION OF THE INVENTION

Figure 1:
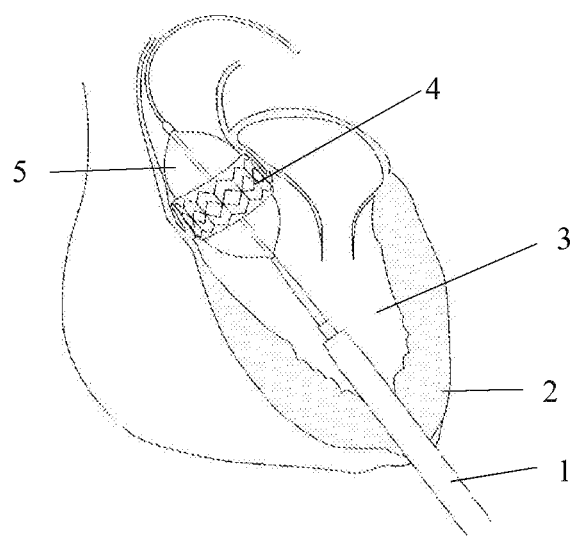
FIG. 1 is a schematic illustration of the transapical valve insertion technique.

Reference will now be made to the drawings wherein like reference numerals identify similar structural features or aspects of the subject disclosure. FIG. 1 is a schematic illustration of the transapical valve insertion technique and shows the balloon catheter used to insert new artificial heart valves during Transapical Aortic Valve Implantation (TAAVI) according to the state of the art. Trocar tube 1 is inserted into the left ventricle 3 of the heart through the myocardium 2. A compressed valve prosthesis constructed from a stainless steel stent with an attached artificial valve 4 is placed on the balloon catheter 5, inserted into the apex of the left ventricle, and positioned directly inside the diseased aortic valve. Once in position, the balloon is inflated to secure the valve in place. The balloon is then deflated and removed leaving the new valve to function immediately.

Figure 2:
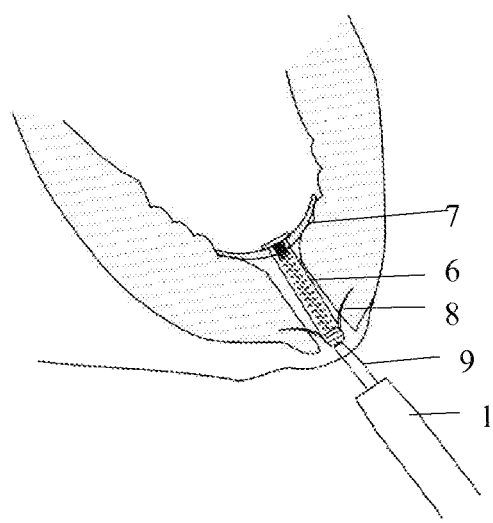
FIG. 2 shows the sealing device, sealing the inner myocardium.

FIG. 2 shows the sealing device sealing the opening in the myocardium. Trocar tube 1, via which the sealing device had been inserted, is retracted behind the ventricular apex. The opening in the tissue is tightly sealed by the membrane coated braiding 7 which is positioned at the inner myocardium at the distal end of the elastic member 6. As shown in the embodiment of FIG. 2, the elastic member 6 includes a coil spring. The braiding 7 is adapted to the anatomical shape of the apex of the left ventricle.

The flexible braiding 7 tightly closes the inner tissue of the heart and is anchored by the fixing member which is operatively associated with the coil spring of elastic member 6. The coil spring is stretched by pulling the double thread 9 down. After the placement of the sealing device, the thread 9 may be removed by pulling down one side of the thread 9 so that the thread 9 may slip out.

Figure 3:
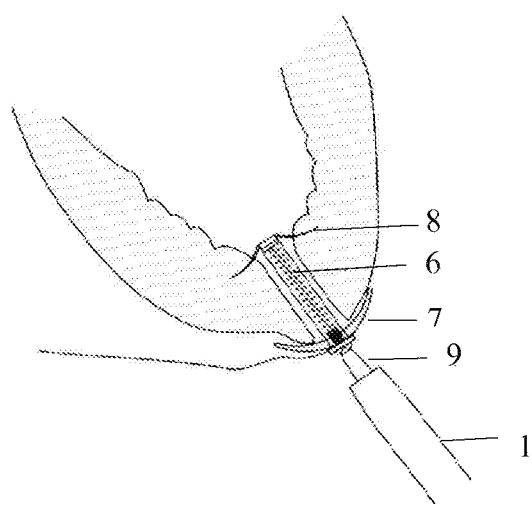
FIG. 3 show the sealing device, sealing the outer myocardium.

FIG. 3 shows the sealing device sealing the outer myocardium. The sealing device can be positioned the other way around as described above should the anatomical shape of the left ventricular apex not allow sealing of the inner myocardium. In this case the membrane coated braiding 7 is positioned at the outer myocardium.

Figure 4:
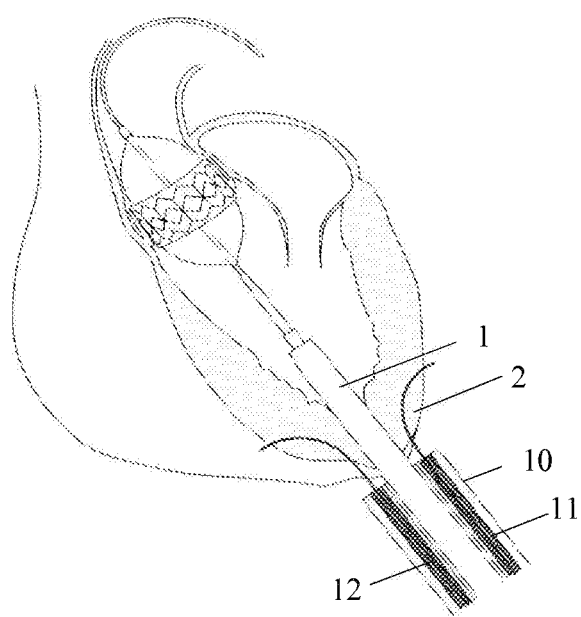
FIG. 4 is a view corresponding to FIG. 1 and in addition shows temporary electrodes inserted for heart stimulation.
Figure 5A:
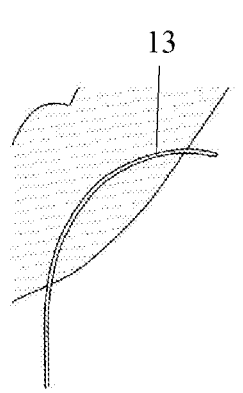
FIGS. 5a to 5d show the placing and the affixing of the stimulation electrodes.
Figure 5B:
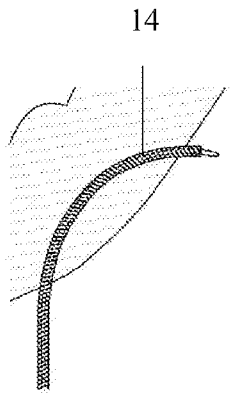
Figure 5C:
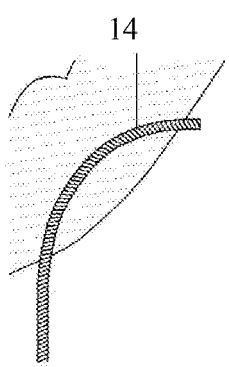
Figure 5D:
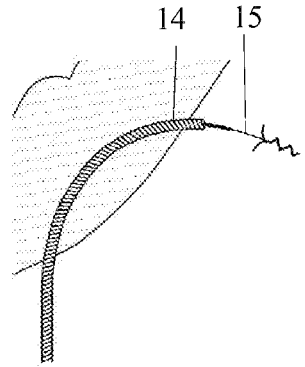

FIG. 4 is a view corresponding to FIG. 1 and in addition shows temporary electrodes (heart wires) inserted for heart stimulation. Heart wires are normally placed in open heart surgical procedures and are attached to the epicardium to synchronize the heart after the surgery. The embodiment according to FIG. 4 provides a possibility to attach heart wires even if the heart is not exposed.

An additional catheter 10 is slipped over the trocar tube 1. The catheter 10 is a three-lumen device which comprises a tubular body defining a first inner lumen extending longitudinally there-through for slipping the catheter over the trocar tube and a second and third lumen 11, 12 which run along each side of the inner lumen allowing temporary electrodes to pass therethrough. A Nitinol-stylet 13, which is preferably pre-shaped, is first inserted within said lumen for assisting in steering of the stimulation electrode when implanted.

FIGS. 5a to 5d show insertion of an electrode within the myocardium of the heart. A pre-shaped stylet 13 is first inserted within lumen 11 or 12 and guided from outside of the heart into and through the myocardium. The tip of the stylet 13 leaves the tissue of the myocardium. A coil 14 is then guided over the stylet towards its tip. The stylet 13 is then withdrawn and the temporary electrode 15 is inserted via the lumen of the coil 14. The proximal portion of electrode 15 is connected to an external pacemaker. The stimulating procedure is the same procedure as the placing of heart wires which are used in open heart surgical procedures if it is expected that the patient will need stimulation for a limited time after the surgery. After completion of temporary stimulation the heart wires are removed by pulling.

Figure 6:
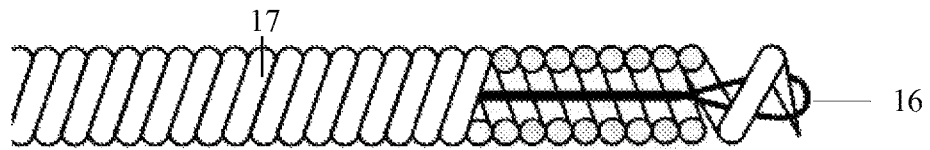
FIG. 6 shows a stimulation electrode in detail.

FIG. 6 shows a stimulation electrode comprising, at its distal end, a loop 16 and a fixing member. The stimulation electrode is inserted by means of coil 17.

Figure 7A:
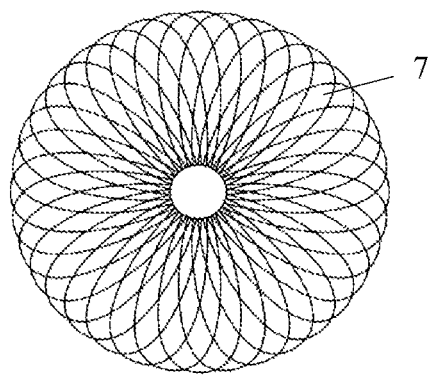
Figure 7B:
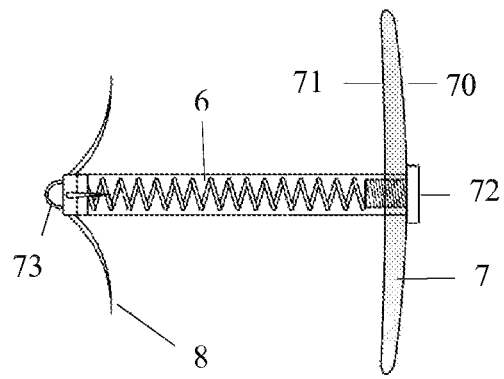

FIGS. 7a, 7b and 7c show the sealing system in detail. FIG. 7a is a top view of the umbrella shaped braiding 7. In some embodiments, the braiding can include about 80 Nitinol threads having a diameter of about 0.1 mm. FIG. 7b is a side view of the sealing device. Coil spring of elastic member 6 is attached to the braiding 7 at its distal end. The fixing member 8 is operatively associated with the coil spring at its proximal end. Loop 73 allows double thread 9 to pass therethrough. Socket 72 may hold the ends of the braiding threads. In unfolded condition the braiding 7 can be umbrella shaped or any other suitable shape. The coating is positioned at the outside face 70 or at the inside face 71 of the braiding 7, preferably at the outside face. If desired, both sides of the braiding 7 may be coated. FIG. 7c shows the braiding 7 in the shape adapted to the anatomical shape of the apex of the left ventricle as shown in use in FIG. 2.

Figures 8A, 9A, 10A:
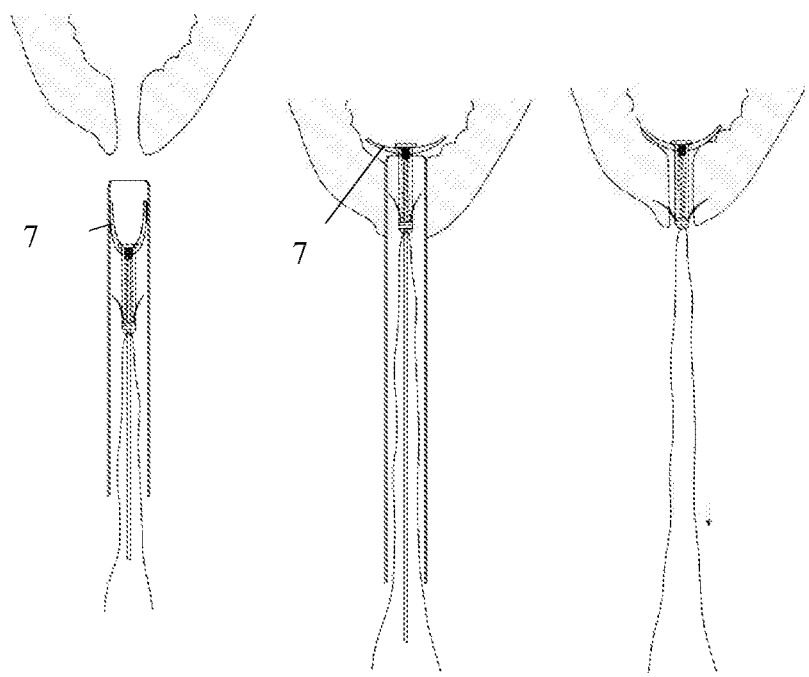

FIGS. 8, 9, and 10 show the steps of placing and affixing the sealing system. FIG. 8 shows the sealing device positioned inside trocar tube 1 before placing the device into the left ventricle. Braiding 7 and fixing member 8 are folded. The stick 20 is for pushing out the sealing device. The folding may be upwards (FIG. 8) or downwards (FIG. 8a).

FIGS. 9 and 9a show the trocar tube placed in the myocardium functioning as a portal for the subsequent placement of the sealing device. The braiding 7 is pushed out of the trocar tube 1 and is unfolded. The fixing member 8 is inside the tube 1 and thus still protected. FIGS. 9 and FIG. 9a differ in the anatomical shape of the apex of the left ventricle and show the adaption of the shape of the braiding 7 to the different anatomical shapes.

FIGS. 10 and 10a show the sealing device placed and the trocar tube 1 removed. By pulling double thread 9 downwards coil spring of the elastic member 6 is pre-stretched. The pre-stretched coil spring is pulled downwards out of the opening in the myocardium. After removing the trocar tube 1 whereby the double thread is still stretched the fixing member 8 moves from a folded into a deployed position and anchors in the myocardium tissue.

Figure 11:
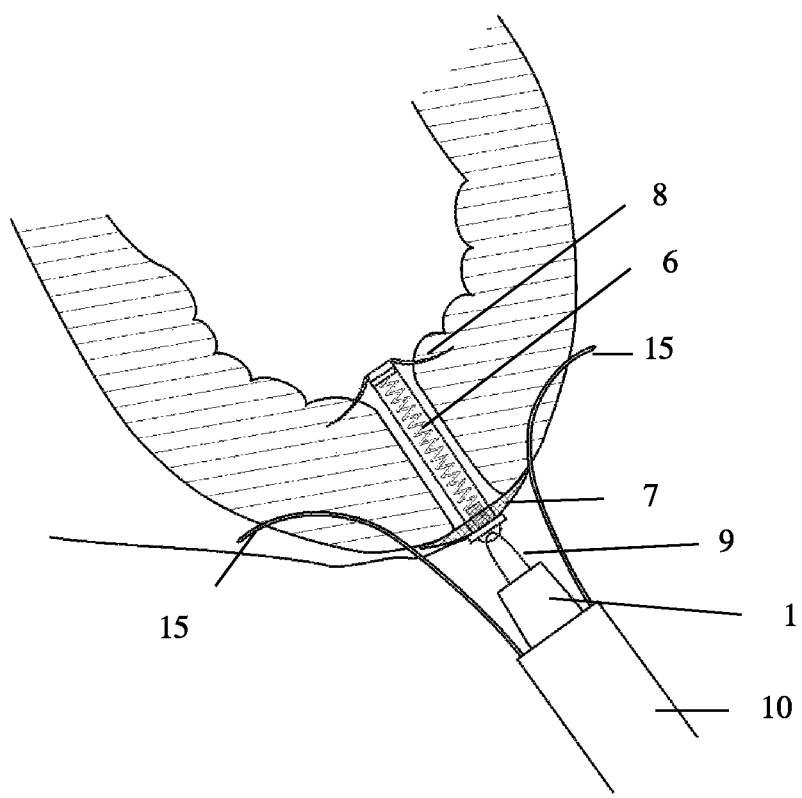
FIG. 11 is a schematic view that shows an embodiment of a device having an umbrella shaped braiding placed at the proximal part of the apical opening and also having electrodes for inserting into the heart tissue.

FIG. 11 shows an embodiment of a device having an umbrella shaped braiding 7 placed at the proximal part of the apical opening and also having electrodes 15 for inserting into the heart tissue. The sealing device can include a membrane coated umbrella shaped braiding 7, an elastic member 6, a fixing member 8, and a double thread 9, e.g., similar to as described above. The device can also include a multi-lumen (e.g., three lumen) catheter 10 slipped over the trocar 1 and one or more temporary electrodes 15 (e.g., two electrodes 15) extending from the catheter 10. The membrane coated braiding 7 can be placed at the proximal end of the elastic member 6. The one or more electrodes 15 can be inserted by using multi-lumen catheter 10 slipped over the trocar 1.

Figure 12:
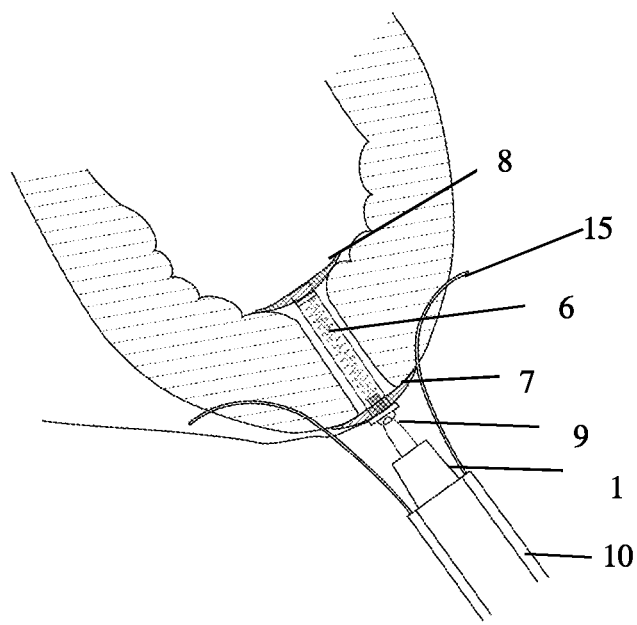
FIG. 12 is a schematic view that shows an embodiment of a device in accordance with this disclosure having a multi-lumen (e.g., three lumen) catheter slipped over the trocar and one or more temporary electrodes.

FIG. 12 shows an embodiment of a device including a membrane coated umbrella shaped braiding 7, an elastic member 6, a fixing member 8, a double thread 9, e.g., similar as described above, a multi-lumen (e.g., three lumen) catheter 10 slipped over the trocar 1, and one or more temporary electrodes 15. In the embodiment of FIG. 12, different from the embodiment of FIG. 11, the fixing member 8 is a second braiding which anchors to the tissue by being pressed against the tissue. The membrane coated braiding 7 can be placed at the proximal end of the elastic member 6. The one or more electrodes 15 can inserted through the multi-lumen catheter 10 slipped over the trocar 1.

Figure 13B:
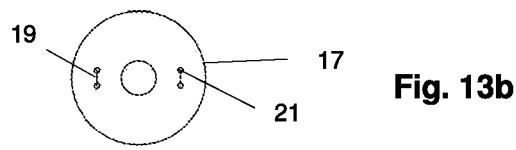
FIGS. 13b and 13c show a plan view of embodiments of a distal disc and proximal disc in accordance with this disclosure, respectively, shown isolated from their respective braiding.
Figure 13A:
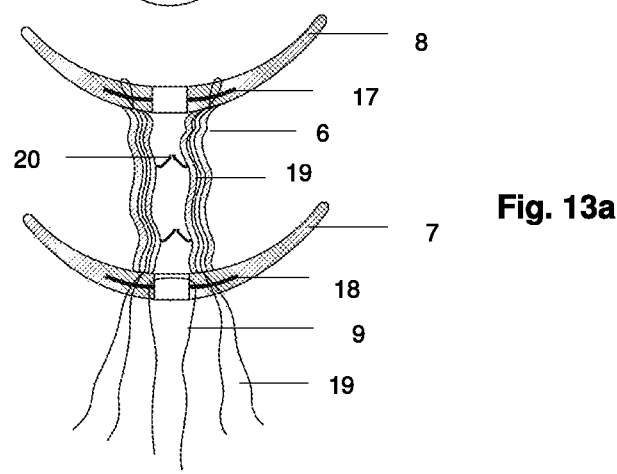
FIG. 13a shows a cross-sectional schematic view of an embodiment of a sealing device in accordance with this disclosure.

FIG. 13a shows an embodiment of a sealing device comprising a membrane coated umbrella shaped braiding 7 placed at the proximal end, an elastic member 6, and a fixing member 8 (e.g., in the form of an umbrella shaped braiding as shown). The fixing member can include surgical threads 9 drawn through the elastic member 6. The sealing can be achieved by pulling the thread, thus pressing the umbrella shaped braiding of the fixing member 8 firmly onto the tissue. The braiding can be coated by a membrane in certain embodiments. One or more valves 20 can be placed inside the elastic member in certain embodiments, e.g., for safe sealing.

In the embodiment shown, rigid or semi-rigid discs 17, 18 can be disposed in each braiding 7, 8. For example, a distal disc 17 (e.g., as shown separately in FIG. 13b) can be disposed in the distal braiding 8 and a proximal disc 18 (e.g., as shown separately in FIG. 13c) can be disposed in the proximal braiding 7. The discs 17, 18 can be made of plastic or any other suitable material. Each disc 17, 18 can include openings 21 (e.g., any suitable number in any suitable pattern) to pull threads (e.g., threads 19 and/or pull thread 9) through and/or to allow the threads to engage the discs 17 (e.g., to pull on the discs as desired).

For example, a proximal disc pull thread 9 can be drawn through the proximal disk 18 in the proximally placed braiding 7 such that a user can pull the proximal braiding 7, e.g., out of the myocardium before removing the proximal braiding 7 from the trocar 1. One or more openings 21 can be included in the distal disc 17 such that one or more threads 19 can be drawn through the distal disk 17 such that a user can pull on the distal disc 17. The one or more threads 19 (e.g., double threads) can be configured to pull the distal disc 17 and/or the distal braiding 8.

Figure 14:
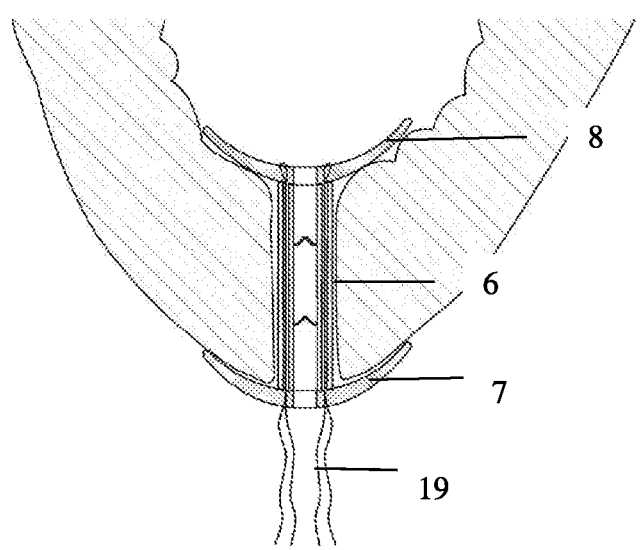
FIG. 14 shows the embodiment of FIG. 13a disposed in heart tissue.

FIG. 14 shows the embodiment of FIG. 13a inserted into heart tissue. To insert the device, a trocar can be inserted via the ventricular apex through the myocardium into the left ventricle. The trocar can include the sealing device as shown in FIG. 13a in a folded state, as appreciated by those having ordinary skill in the art in view of this disclosure. A pusher attached to the proximal braiding 8 can be used to push the device. At first, the distally placed braiding 8 is pushed out and unfolds. The trocar can then be retracted and the pusher can be removed. Pull thread 9 can be used to draw the proximally placed braiding 7 out of the myocardium and to stretch the elastic member 6, e.g., which, as shown, can include a flexible tube like structure (e.g., maid of braiding) with threads 19 drawn through. When the proximally placed braiding 7 is unfolded, threads 19 can be pulled down to press the tissue in between the distal braiding 8 and the proximal braiding 7 together by pulling the distal braiding 8 closer to the proximal braiding 7. The end of the threads 19 can then be knotted to fix the relative position of the proximal braiding member 7 and the distal braiding 8. In certain embodiments, one or more valves 20 can be present inside the elastic member 6 for safe sealing. Any suitable valve types are contemplated herein.

In certain embodiments, e.g., similar as shown in FIGS. 11 and 12, temporary electrodes 15 (e.g., heart wires) may also be inserted when using the above described sealing device of FIG. 13a. In this regard, the one or more of the braidings 7, 8 in any embodiment disclosed hereinabove can function as an indifferent electrode. The braiding 7 or 8 can be thus electrically connected to an external pacemaker. Any other suitable electrical connection is contemplated herein.

In accordance with at least one aspect of this disclosure, a method for sealing a tissue opening includes inserting a trocar tube 1 including a folded sealing device (e.g., as shown in FIG. 13a) disposed within the trocar 1, and guiding the trocar tube (e.g., trocar 1) through an opening in a myocardium into a patient's ventricle. The sealing device can include any suitable embodiment as disclosed herein. For example, the sealing device can include an elongated elastic member 6 having a distal and a proximal end, a proximal umbrella shaped braiding 7 extending radially from the elongated elastic member 6, the proximal braiding being positioned at the proximal end of the elastic member 6, the proximal braiding 7 including a proximal disc 18 disposed therein having a proximal disc thread 9 disposed therethrough such that a user can pull the proximal braiding 7, and a distal umbrella shaped braiding 8 extending radially from the elongated elastic member 6 and being positioned at the distal end of the elastic member 6 opposite to the proximal braiding 7.

The method can include pushing the distal braiding 8 out of the trocar tube 1 so that the distal braiding 8 moves from a folded position into a deployed position to contact an inside tissue wall (e.g., as shown in FIG. 14) while the proximal braiding 7 can remain inside the trocar tube 1.

The method can include stretching the elastic member 6 by pulling the proximal disc thread 9 engaged with the proximal disc 18 such that the proximal braiding 7 is located out of the opening in the myocardium when the proximal braiding 7 is removed from the trocar 1. The method can include removing the proximal braiding from the trocar 1 while the trocar 1 is located out of the opening in the myocardium such that the proximal braiding 7 moves from a folded position into a deployed position and presses against an outside tissue wall (e.g., as shown in FIG. 14).

Removing the proximal braiding 7 can include removing the trocar 1 after the distal braiding 8 is contacting the inside tissue wall. The distal braiding 8 can include a distal disc 17 disposed therein. The sealing device can include one or more threads 19 disposed through the distal disc 17 such that the one or more threads 19 can pull on the distal disc 17 and/or the distal braiding 8. The one or more threads 19 can be two threads 19 (e.g., double threads) as shown, for example. The term "double threads" as used herein can mean a single thread that is passed through the distal disc 17 and brought back around through the proximal end of the device, or actually two separate threads attached to the distal disc 17, or any other suitable definition as appreciated by those having ordinary skill in the art. Any suitable number of threads 9, 19 is contemplated herein. The one or more threads 19 can also be disposed through the proximal disc 18 such that the one or more threads 19 can be pulled through the proximal disc 18 in use.

Figure 13C:
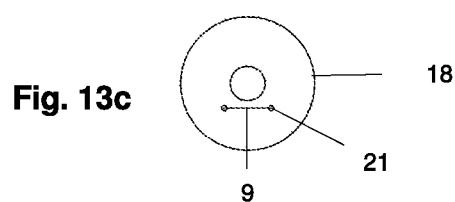

The proximal braiding 7 and/or the distal braiding 8 can include a plurality of fine threads of a memory metal alloy and wherein at least one face is coated by a membrane. Any other suitable construction is contemplated herein. The elastic member 6 can define a tube, for example. As shown in FIGS. 13a and 14, the one or more threads 19 can be disposed in a wall of the elastic member 6 between the proximal end and the distal end of the elastic member 6. The elastic member 6 can include one or more valves 20 disposed within the tube of the elastic member 6. As shown in FIGS. 13b and 13c, the proximal and/or distal discs 18, 17 can include a central hole therethrough to form a washer shape, e.g., to allow fluid communication or instrument insertion through the tube of the elastic member 6 and/or valves 20 therein.

The method can include pulling the one or more threads 19 after removing the proximal braiding 7 from the trocar 1 to press tissue between the distal and proximal braiding 8, 7. In certain embodiments, the method can include knotting the one or more threads 19, e.g., to the proximal disc 18 and/or the proximal braiding 7 to fix the relative position of the distal and proximal braiding 8, 7.

The method can include using a multi-lumen catheter 10 to insert one or more temporary electrodes 15 and the trocar 1 into the myocardium, and stimulating the myocardium using the one or more temporary electrodes 15. The method can include using at least one of the distal braiding 8 or the proximal braiding 7 as an indifferent electrode, e.g., that is electrically connected to an external pacemaker. Any other suitable use of an indifferent electrode is contemplated herein.

While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A method for sealing a tissue opening, comprising:
   inserting a trocar tube including a folded sealing device disposed within the trocar tube, and guiding the trocar tube through an opening in a myocardium into a patient's ventricle, the sealing device comprising:
   an elongated elastic member having a distal and a proximal end;
   a proximal umbrella shaped braiding extending radially from the elongated elastic member, the proximal braiding being positioned at the proximal end of the elongated elastic member, wherein the proximal braiding includes a proximal disc disposed therein having a proximal disc thread disposed therethrough such that a user can pull the proximal braiding; and
   a distal umbrella shaped braiding extending radially from the elongated elastic member and being positioned at the distal end of the elongated elastic member opposite to the proximal braiding;
   pushing the distal braiding out of the trocar tube so that the distal braiding moves from a folded position into a deployed position to contact an inside tissue wall, whereas the proximal braiding remains inside the trocar tube;
   stretching the elongated elastic member by pulling the proximal disc thread engaged with the proximal disc such that the proximal braiding is located out of the opening in the myocardium when the proximal braiding is removed from the trocar tube; and
   removing the proximal braiding from the trocar tube while the trocar tube is located out of the opening in the myocardium such that the proximal braiding moves from a folded position into a deployed position and presses against an outside tissue wall.

2. The method of claim 1, wherein removing the proximal braiding includes removing the trocar tube after the distal braiding is contacting the inside tissue wall.

3. The method of claim 1, wherein the distal braiding includes a distal disc disposed therein.

4. The method of claim 3, wherein the sealing device further comprises one or more threads disposed through the distal disc such that the one or more threads can pull on the distal disc and/or the distal braiding.

5. The method of claim 4, wherein the one or more threads includes two threads.

6. The method of claim 4, wherein the one or more threads are also disposed through the proximal disc such that the one or more threads can be pulled through the proximal disc.

7. The method of claim 6, further comprising pulling the one or more threads after removing the proximal braiding from the trocar tube to press tissue between the distal and proximal braiding.

8. The method of claim 7, further comprising knotting the one or more threads to the proximal disc and/or the proximal braiding to fix the relative position of the distal and proximal braiding.

9. The method of claim 1, further comprising using a multi-lumen catheter to insert one or more temporary electrodes and the trocar tube into the myocardium, and stimulating the myocardium using the one or more temporary electrodes.

10. The method of claim 9, further comprising using at least one of the distal braiding or the proximal braiding as an indifferent electrode electrically connected to an external pacemaker.

11. A tissue sealing device, comprising:
an elongated elastic member having a distal and a proximal end;
a proximal umbrella shaped braiding extending radially from the elongated elastic member, the proximal braiding being positioned at the proximal end of the elongated elastic member, wherein the proximal braiding includes a proximal disc disposed therein having a proximal disc thread disposed therethrough such that a user can pull the proximal braiding; and
a distal umbrella shaped braiding extending radially from the elongated elastic member and being positioned at the distal end of the elongated elastic member opposite to the proximal braiding.

12. The device of claim 11, wherein the distal braiding includes a distal disc disposed therein.

13. The device of claim 12, wherein the sealing device further comprises one or more threads disposed through the distal disc such that the one or more threads can pull on the distal disc and/or the distal braiding.

14. The device of claim 13, wherein the one or more threads includes two threads.

15. The device of claim 14, wherein the two threads include double threads.

16. The device of claim 13, wherein the one or more threads are also disposed through the proximal disc such that the one or more threads can be pulled through the proximal disc.

17. The device of claim 16, wherein the elongated elastic member defines a tube.

18. The device of claim 17, wherein the one or more threads are disposed in a wall of the elongated elastic member between the proximal end and the distal end of the elongated elastic member.

19. The device of claim 17, wherein the elongated elastic member includes one or more valves disposed within the tube.

20. The device of claim 17, wherein the proximal and/or distal discs include a central hole therethrough to form a washer shape.

* * * * *